(12) United States Patent
Forstner et al.

(10) Patent No.: US 7,095,491 B2
(45) Date of Patent: Aug. 22, 2006

(54) DEVICE AND METHOD FOR MEASURING CONSTITUENTS IN BLOOD

(75) Inventors: Klaus Forstner, Tamm (DE); Bernd Schöller, Karlsruhe (DE)

(73) Assignee: MCC Gesellschaft für Diagnosesysteme in Medizin und Technik mbH & Co. KG, Karlsruhe (DE)

( * ) Notice: Subject to any disclaimer, the term of this patent is extended or adjusted under 35 U.S.C. 154(b) by 0 days.

(21) Appl. No.: 10/509,001

(22) PCT Filed: Feb. 8, 2003

(86) PCT No.: PCT/DE03/00372

§ 371 (c)(1),
(2), (4) Date: Sep. 24, 2004

(87) PCT Pub. No.: WO03/079899

PCT Pub. Date: Oct. 2, 2003

(65) Prior Publication Data

US 2005/0168722 A1 Aug. 4, 2005

(51) Int. Cl.
*G01N 33/48* (2006.01)
(52) U.S. Cl. .................................................... 356/39
(58) Field of Classification Search .......... 356/39–42, 356/335–343
See application file for complete search history.

(56) References Cited

U.S. PATENT DOCUMENTS

| | | | |
|---|---|---|---|
| 3,511,227 A * | 5/1970 | Johnson | 600/479 |
| 4,086,915 A * | 5/1978 | Kofsky et al. | 600/330 |
| 4,679,939 A * | 7/1987 | Curry et al. | 356/336 |
| 5,178,142 A * | 1/1993 | Harjunmaa et al. | 600/310 |
| 5,188,108 A * | 2/1993 | Secker | 600/310 |
| 5,386,819 A | 2/1995 | Kaneko et al. | |
| 5,427,920 A * | 6/1995 | Berndt et al. | 435/34 |
| 5,664,574 A | 9/1997 | Chance | |
| 5,710,630 A * | 1/1998 | Essenpreis et al. | 356/479 |
| 5,770,454 A * | 6/1998 | Essenpreis et al. | 436/164 |
| 6,064,898 A | 5/2000 | Aldrich | |
| 6,149,588 A | 11/2000 | Noda et al. | |
| 6,151,517 A | 11/2000 | Honigs et al. | |
| 6,151,518 A | 11/2000 | Hayashi | |
| 6,226,540 B1 * | 5/2001 | Bernreuter | 600/323 |
| 6,522,398 B1 * | 2/2003 | Cadell et al. | 356/39 |

FOREIGN PATENT DOCUMENTS

| | | |
|---|---|---|
| DE | 196 09 410 A1 | 9/1997 |
| DE | 196 12 425 C2 | 8/2000 |
| DE | 100 15 622 A1 | 10/2001 |
| DE | 196 51 690 C2 | 12/2001 |
| EP | 0074428 | 3/1983 |

(Continued)

Primary Examiner—Gregory J. Toatley, Jr.
Assistant Examiner—Isiaka O. Akanbi
(74) Attorney, Agent, or Firm—Friedrich Kueffner

(57) ABSTRACT

The method and device serve to measure a proportion of constituents in blood. To this end, electromagnetic radiation of different radiation wavelengths is directed through a tissue (9) containing blood vessels (1). At least a portion of the radiation exiting the vessel is detected using sensors, and a corresponding measured value derived therefrom is fed to an evaluating device. The evaluating device (10) is connected to at least two sensors (2, 3, 4) and has an analyzer (11) for determining a dispersion of radiation by evaluating the intensity of the radiation received by the individual sensors. An individual calibration determination is carried out by evaluating the angle-dependent dispersion and can be drawn upon for conducting a pulse spectroscopic determination of concentrations of substances.

21 Claims, 10 Drawing Sheets

FOREIGN PATENT DOCUMENTS

| | | |
|---|---|---|
| WO | 8901758 | 3/1989 |
| WO | 9939631 | 8/1999 |
| WO | 0016688 | 3/2000 |
| WO | 0042905 | 7/2000 |
| WO | 0062661 | 10/2000 |
| WO | 0062670 | 10/2000 |
| WO | 0228274 | 4/2002 |

* cited by examiner

DEVICE AND METHOD FOR MEASURING CONSTITUENTS IN BLOOD

The invention concerns a method for controlling a device for measuring quantitative-proportions of blood constituents, in which electromagnetic radiation of different radiation frequencies is passed through a blood-containing vessel, and in which at least a portion of the radiation exiting the vessel is detected by sensors and fed to an evaluating device.

The invention also concerns a device for measuring quantitative proportions of blood constituents, which has at least one emission source for generating electromagnetic radiation and at least one sensor, which detects the transmitted portion of the radiation and is connected to an evaluating device.

Methods and devices of these types are already known in various embodiments. For example, U.S. Pat. No. 6,151,518 describes a device for determining the concentrations of certain blood constituents, in which a part of the living organism is transilluminated by a light source, and the portion of the light that is transmitted by the organism is detected by measurement techniques and fed to an evaluating device. A comparable method is also described in PCT-WO 00/42905. Another system is described in PCT-WO 99/39631. In this system, a measurement device is positioned next to an index finger, which is transilluminated with a plurality of light sources, and the reflected components are determined. Similar systems for the detection of blood constituents by measurement techniques involving the use of a finger as the site of measurement are explained in U.S. Pat. No. 6,064,898 and U.S. Pat. No. 6,149,588.

A device for measuring the hemoglobin concentration of blood is described in DE Patent 196 12 425, and another device involving the use of measurement in the area of the finger is explained in PCT-WO 89/01758.

A measuring device for the noninvasive determination of the hemoglobin concentration of blood is already known from the publication "Jahrestagung der Gesellschaft für Biomedizinische Meßtechnik e.V. [Annual Conference of the Society for Biomedical Measuring Technique], Sep. 28–30, 2000 in Lübeck, Vol. 45, Kraitl, Behrens, Hornberger, Gehring".

All prior-art devices have the disadvantage that they are subjected to a standard calibration based on a collection of persons that was selected during the development of the given devices. This can result in relatively high measurement inaccuracy when the device is used for an individual patient, since the individual histoanatomy with respect to the radiation transmission of the given patient could not be taken into consideration in the general calibration. So far, in many cases, only a relative change in the spectroscopically measured substance concentrations can be determined.

Therefore, the objective of the present invention is to specify a method of the aforementioned type that allows increased measurement accuracy and automatic determination of the individual characteristics of the patient, so that an absolute measurement can be made, i.e., a measurement that is tied to units and is not merely a relative measurement.

This objective is achieved by positioning at least two radiation detection sensors a certain distance apart and by assigning to the evaluating device a calibration characteristic curve, which is determined by an individual calibration measurement, in which at least one constant is used as the calibration criterion and is determined from at least one measured variable detected by the sensors.

A further objective of the invention is to design a device of the aforementioned type in such a way that improved measuring quality is achieved.

In accordance with the invention, this objective is achieved by providing the evaluating device with at least two sensors and with an analyzer for determining the angle-dependent scattering of the radiation by evaluating the signals received from the individual sensors.

A significant increase in measurement accuracy can be achieved by the individual detection of the tissue-dependent scattering. There is only an insignificant increase in the apparatus expense. The time required for the measurement is no greater.

With respect to measurement technology, the scattering can be determined in an especially reliable way by the use of at least three receiving elements.

An especially simple design with respect to measurement technology can be achieved by using electromagnetic radiation in the visible and infrared frequency range.

The measurement can be performed by the methods of multiwave pulse spectroscopy.

Individualized patient calibration can be carried out without prolonging the measuring time for a blood parameter by determining the spatial scattering of the radiation by measurement technology.

To this end, it is necessary to determine the scattering by determining a radiation intensity that deviates from the primary irradiation direction.

To allow compensation of changes in parameters (e.g., change in sensor position, patient movements) during the performance of the measurement, it is proposed that a periodic calibration be carried out during the performance of the measurement.

An especially simple evaluation criterion can be implemented by determining the scattering by an analysis of the pulse-cyclical signals of the measured values of the individual sensors.

A preferred application is the determination of the oxygen concentration of the blood.

In addition, there is the possibility of determining oxygen concentration relative to a reference quantity in the blood.

It is also possible to determine an absolute oxygen concentration of the blood.

A symmetrical measurement setup can be achieved by arranging the sensors at essentially equal distances from one another. This setup is a special case of a general arrangement in which this condition is not satisfied.

Specific embodiments of the invention are schematically illustrated in the drawings.

Figure 1:
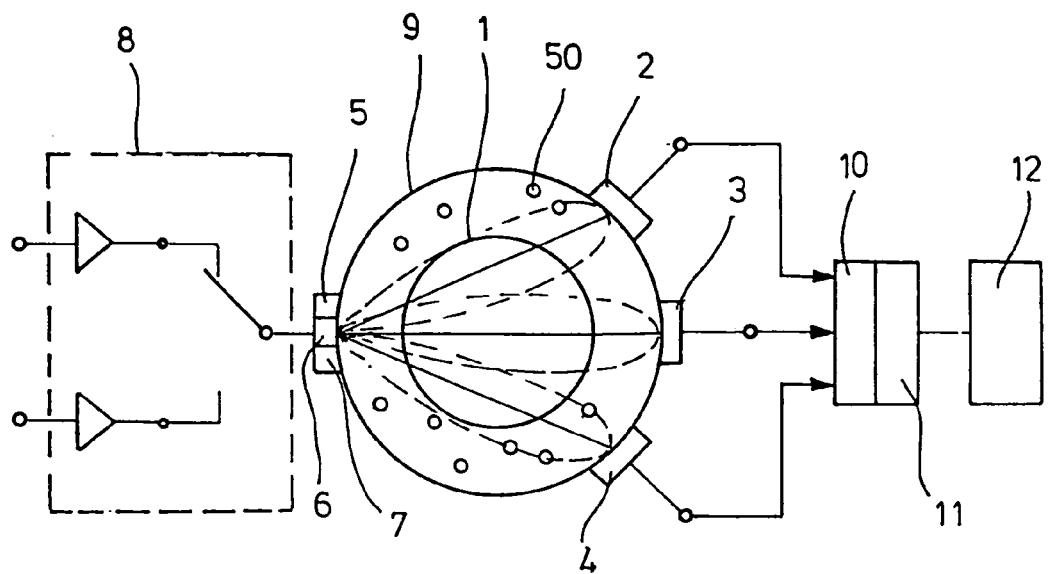
FIG. 1 shows a schematic diagram of a measuring setup.

In the embodiment in FIG. 1, which shows a cross section of a tissue (9) with vessels (1, 50), three sensors (2, 3, 4) and three emission sources (5, 6, 7) are arranged around the blood-conveying tissue (9). The emission sources (5, 6, 7) can be realized, for example, as light-emitting diodes or laser diodes. Photodiodes can be used as the sensors (2, 3, 4).

The emission sources (5, 6, 7) are connected to a multiplexer (8) for sequential control. The sensors (2, 3, 4) and the emission sources (5, 6, 7) are preferably placed directly on the external surface of the tissue (9) that surrounds the vessel (1, 50). The sensors (2, 3, 4) are connected to an evaluating device (10), which is provided with an analyzer (11). Measurement results made available by the evaluating device (10) can be visualized or printed out in the area of a display device (12), and electronic transmission to devices for further processing of the measured values is also possible.

Figure 2:
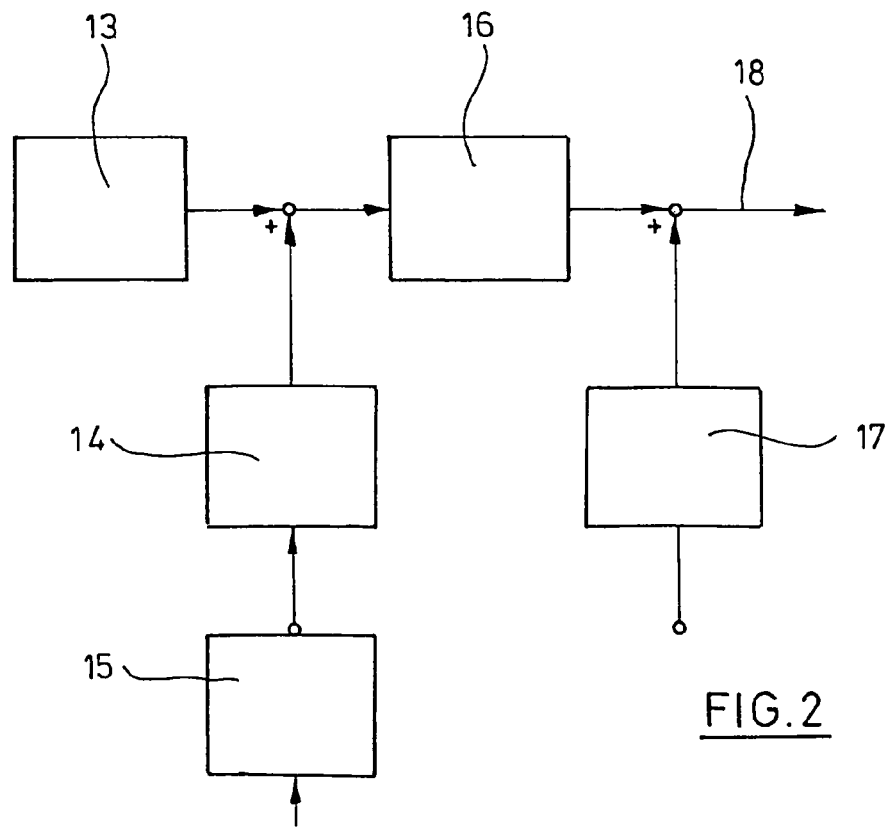
FIG. 2 shows a schematic block diagram for illustrating an individual calibration.

The block diagram in FIG. 2 shows schematically the sequence of an individual calibration. A standard calibration function (13) is used to establish, initially a priori, a patient-independent basic setting, which is then combined with a scattering determination (14), which is connected to a measuring device (15), during the performance of the measuring procedure for the individual patient. The measuring device (15) detects the signals of those sensors (2, 3, 4) that are not assigned to an actual primary irradiation direction of the associated emission source (5, 6, 7). The results of the standard calibration function (13) and the output value of the scattering determination (14) are combined with each other by a combiner (16) according to an algorithm preset as an individual calibration function. An output value of the combiner (16) is combined with a measurement variable (17), which is determined from the measured value of that sensor (2, 3, 4) which lies in the primary irradiation direction of the associated emission source (5, 6, 7). Combination of the output value of the combiner (16) and the measurement variable (17) yields the respective target quantity (18).

Figure 3:
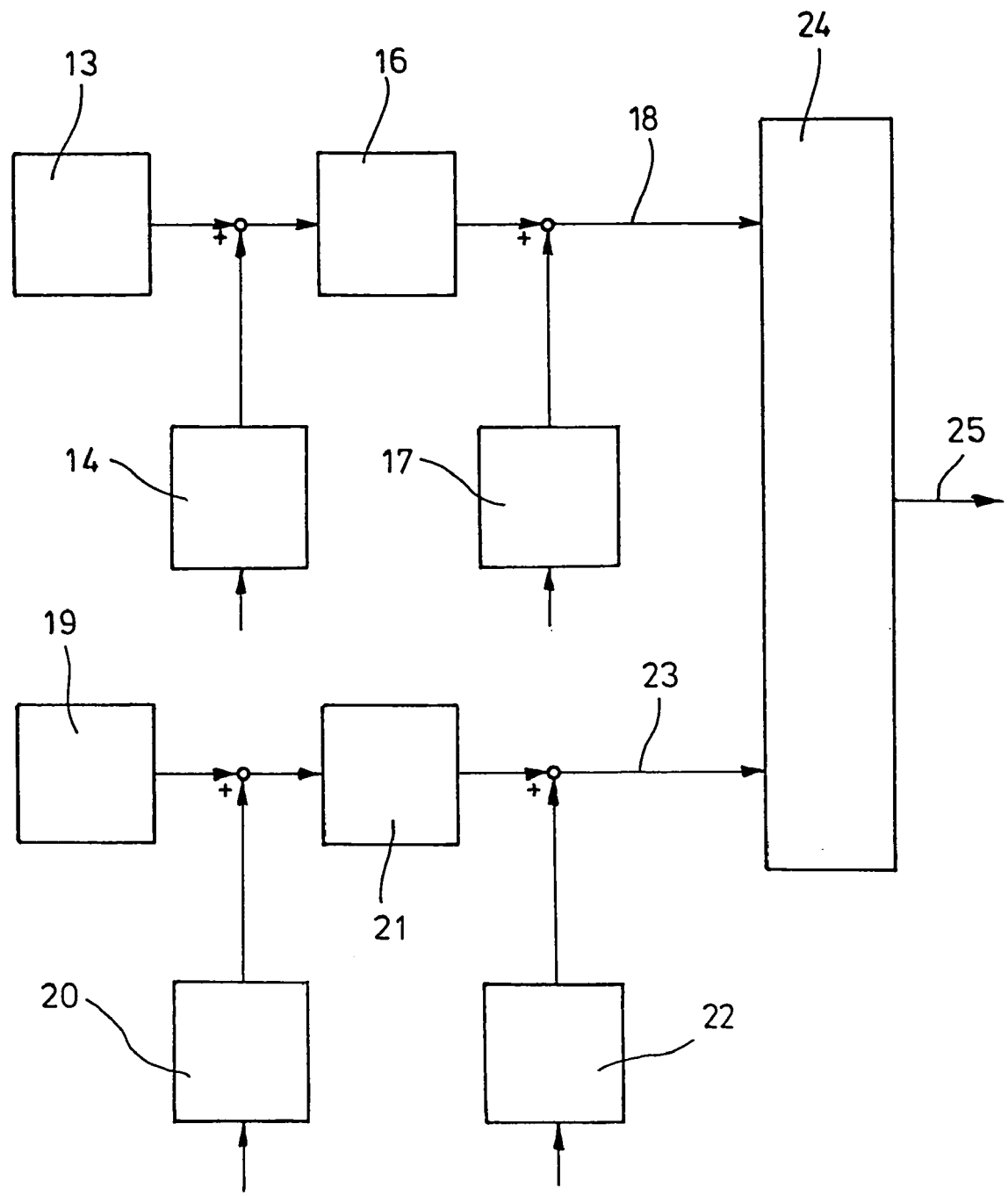
FIG. 3 shows a schematic block diagram for illustrating the determination by measurement technology of a hemoglobin concentration or oxygen saturation of the blood.

FIG. 3 shows a block diagram for explaining an optical hemoglobin measurement for determining the oxygen content of the blood. This measuring technique is based on the fact that hemoglobin with bound oxygen shows different optical absorption behavior from hemoglobin without bound oxygen.

Basically, the block diagram in FIG. 3 consists of two functional components of the type shown in FIG. 2. In this case, the system consisting of the standard calibration function (13), the scattering determination (14), the combiner (16), and the measurement variable (17) is connected in parallel with another system consisting of a standard calibration function (19), a scattering determination (20), a combiner (21) and a measurement variable (22). The target quantity (18) and the target quantity (23), which is the output value of the second system, are brought together at an interconnection (24), which supplies a resulting target quantity (25) as an output value.

Figure 4:
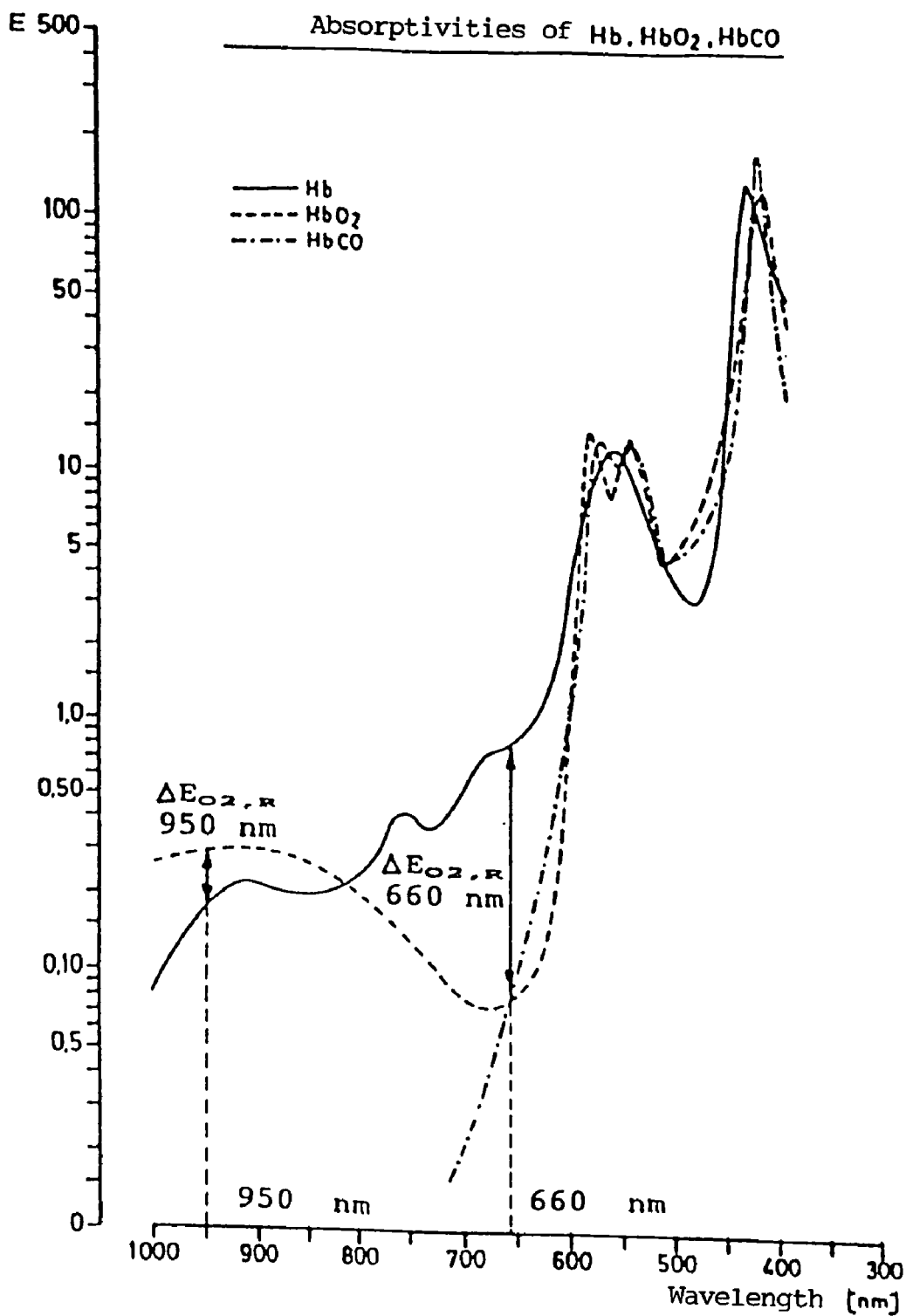
FIG. 4 shows a typical absorption spectrum in optical hemoglobin measurement.
Figure 5:
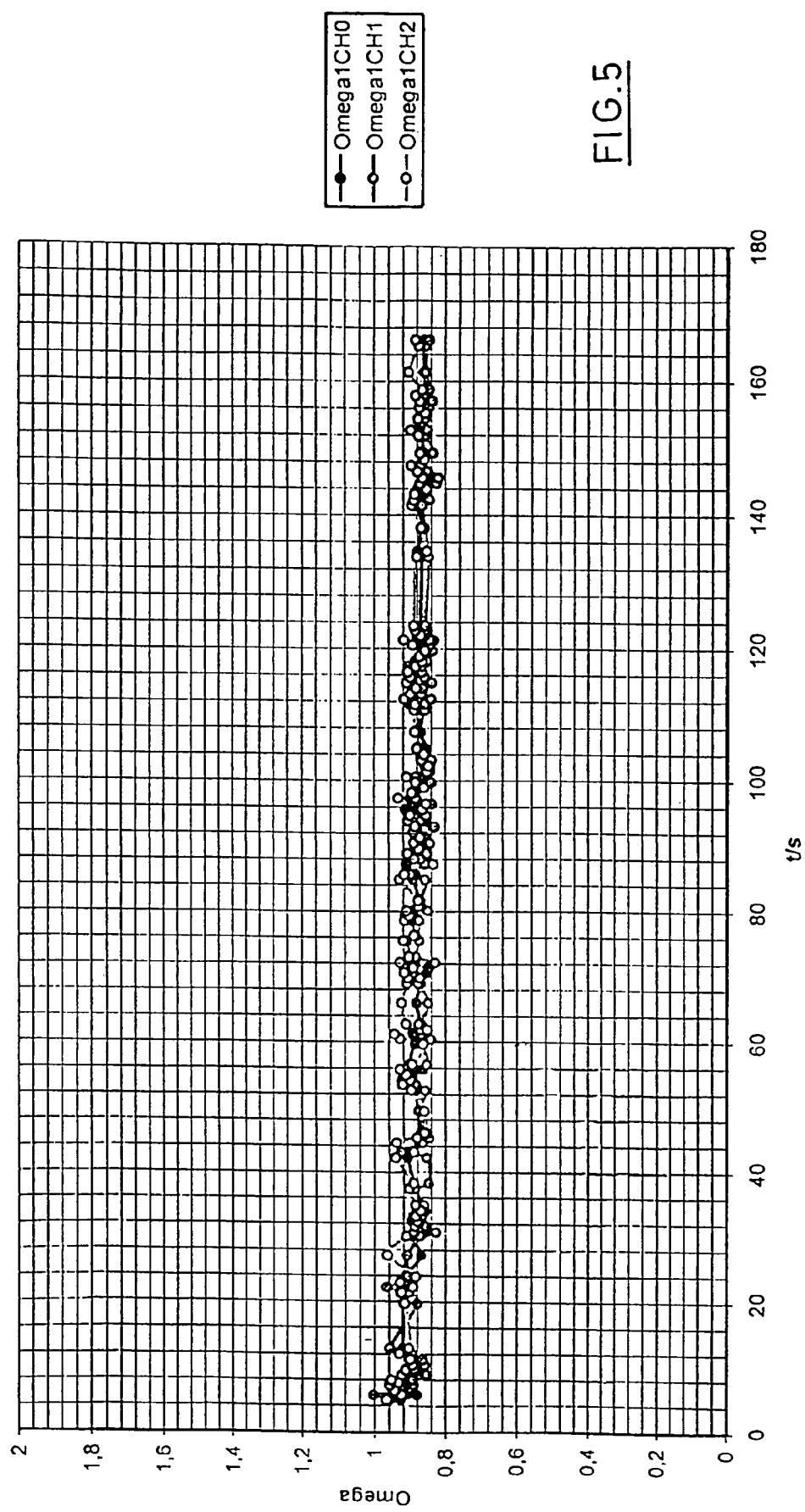
FIG. 5 shows the measurement variable omega for three measuring channels as a function of time.
Figure 6:
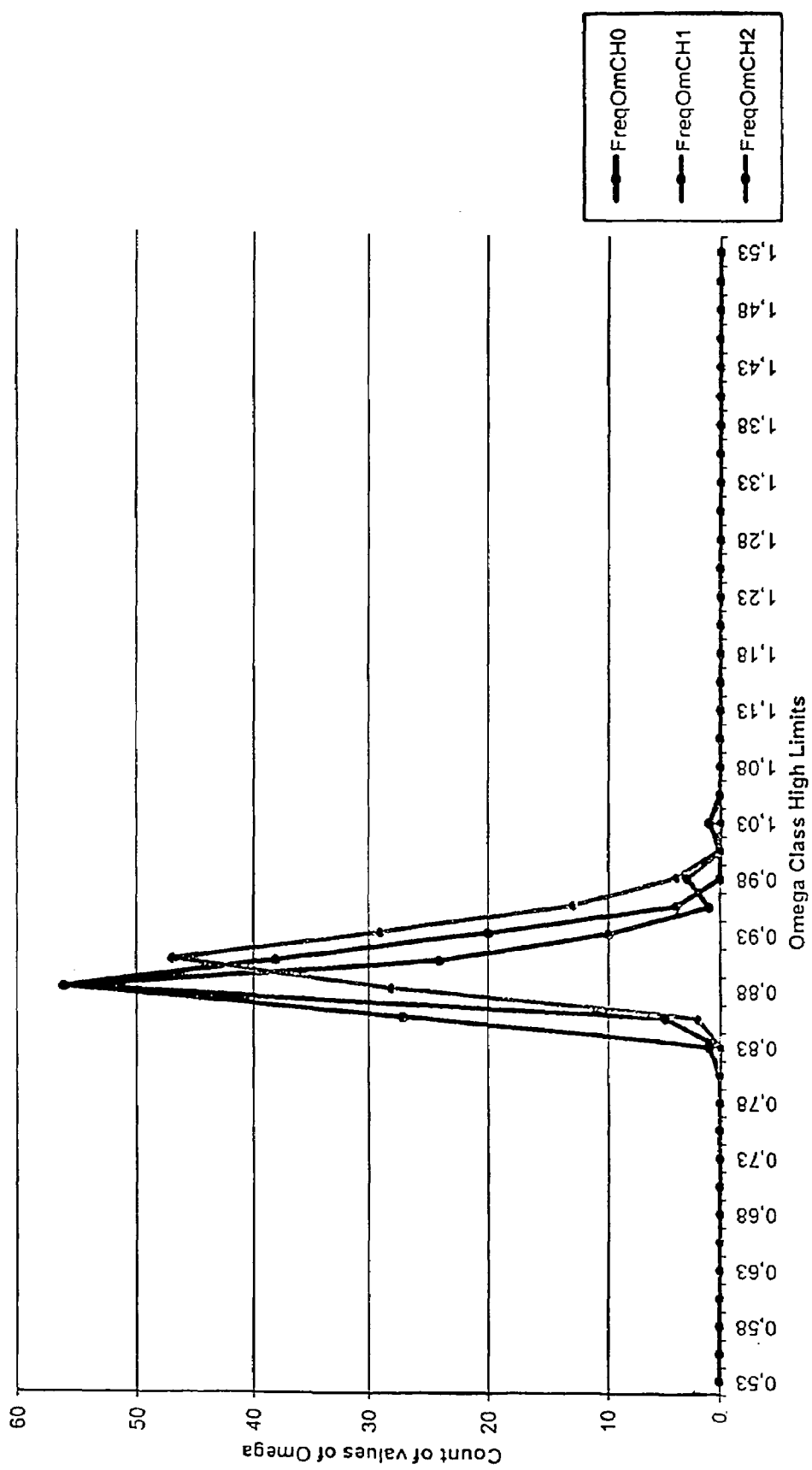
FIG. 6 shows a histogram of the measurement variable omega for three measuring channels.
Figure 7:
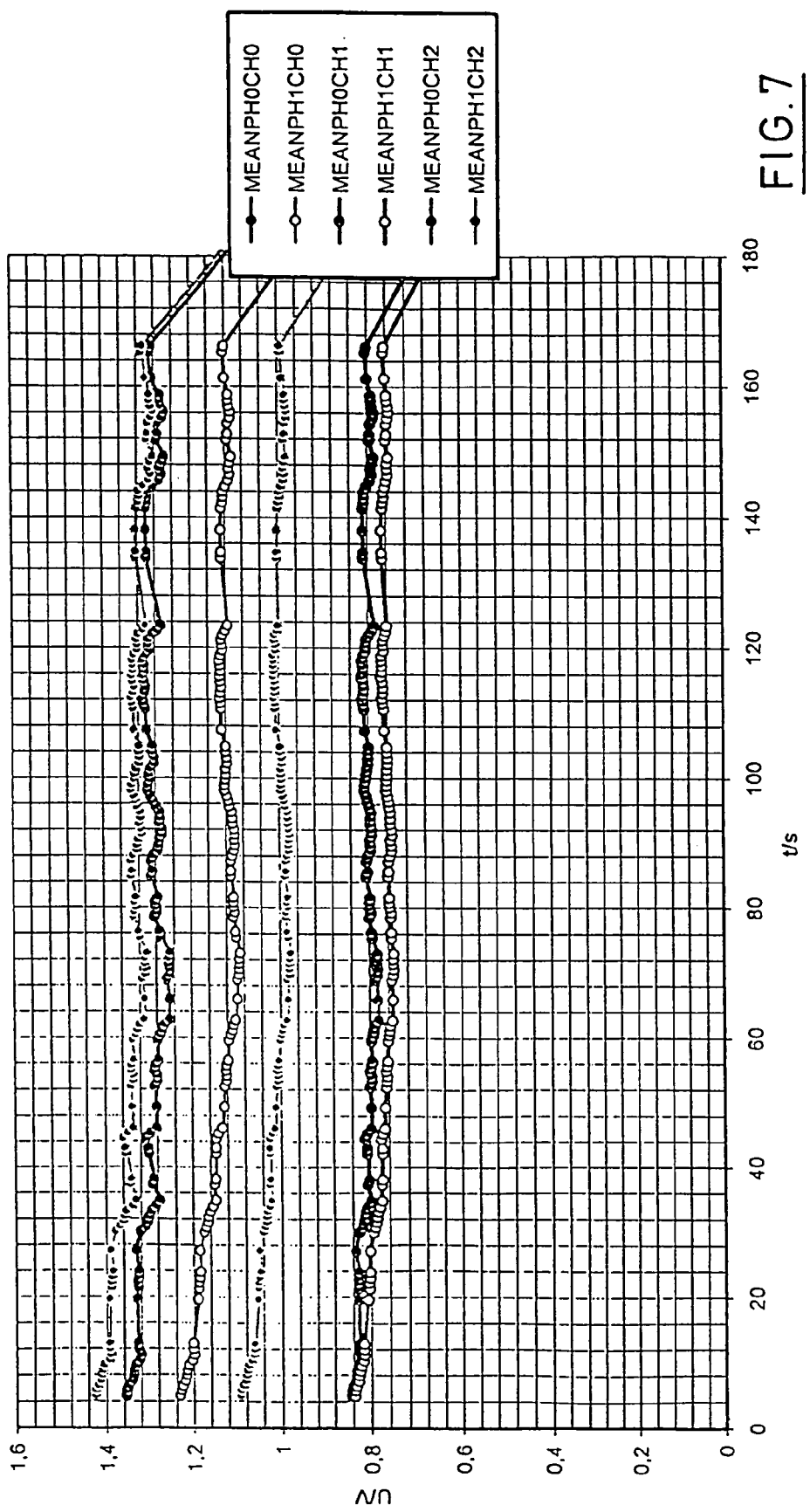
FIG. 7 shows intensities for the three measuring channels for two variables each.
Figure 8:
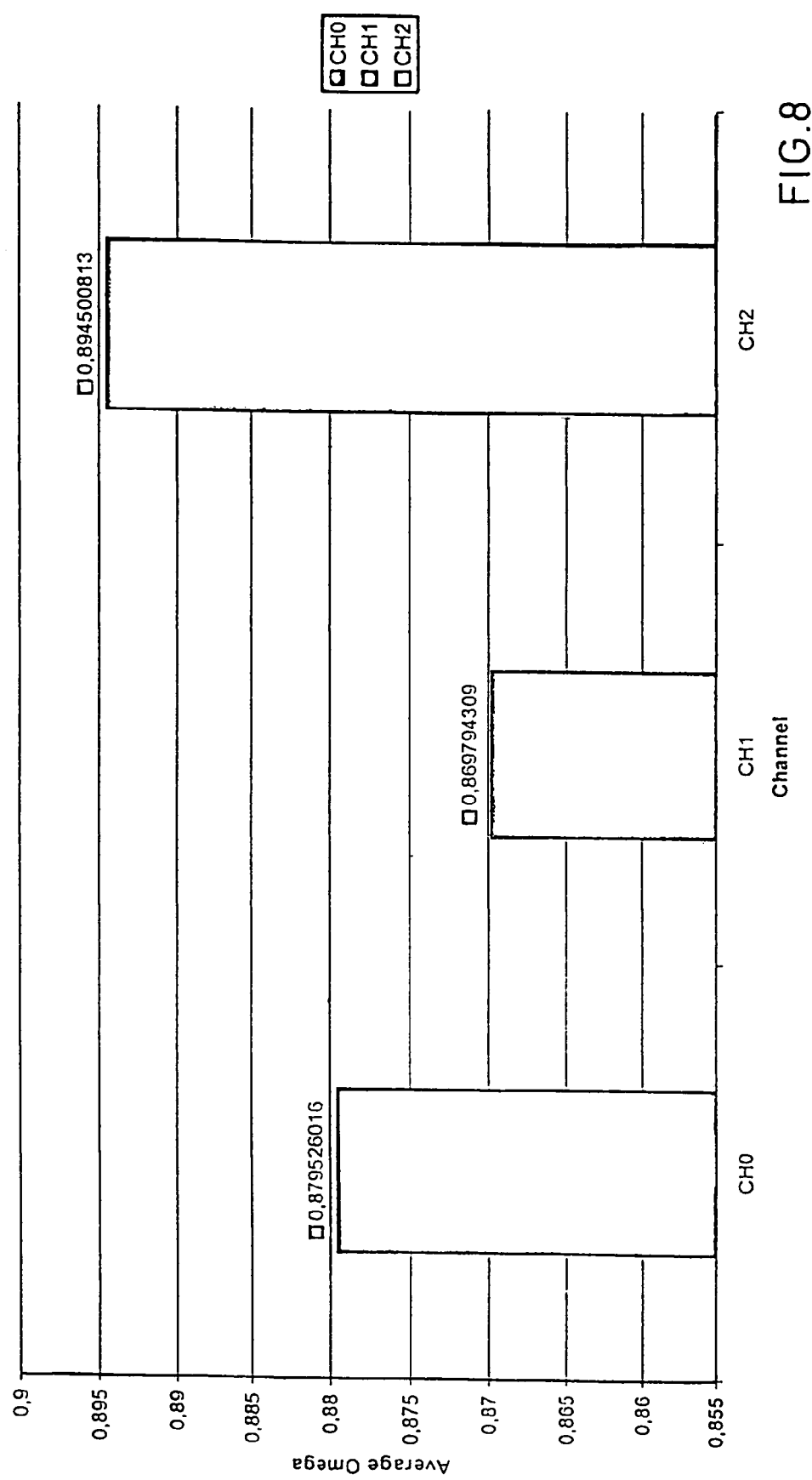
FIG. 8 shows mean values of the measuring variable omega for the three measuring channels.
Figure 9:
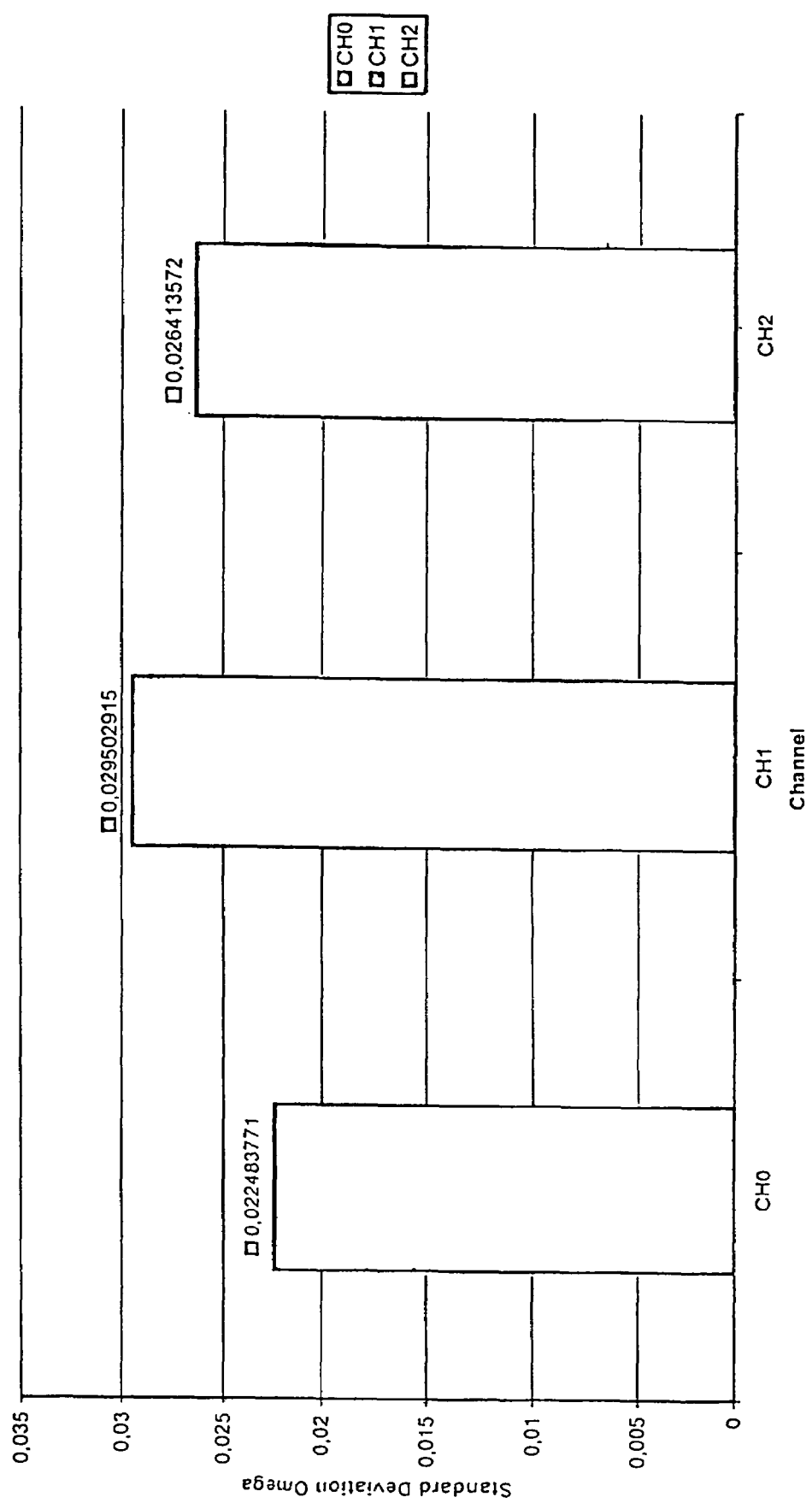
FIG. 9 shows determined standard deviations of the measurement variable omega for the three measuring channels.
Figure 10:
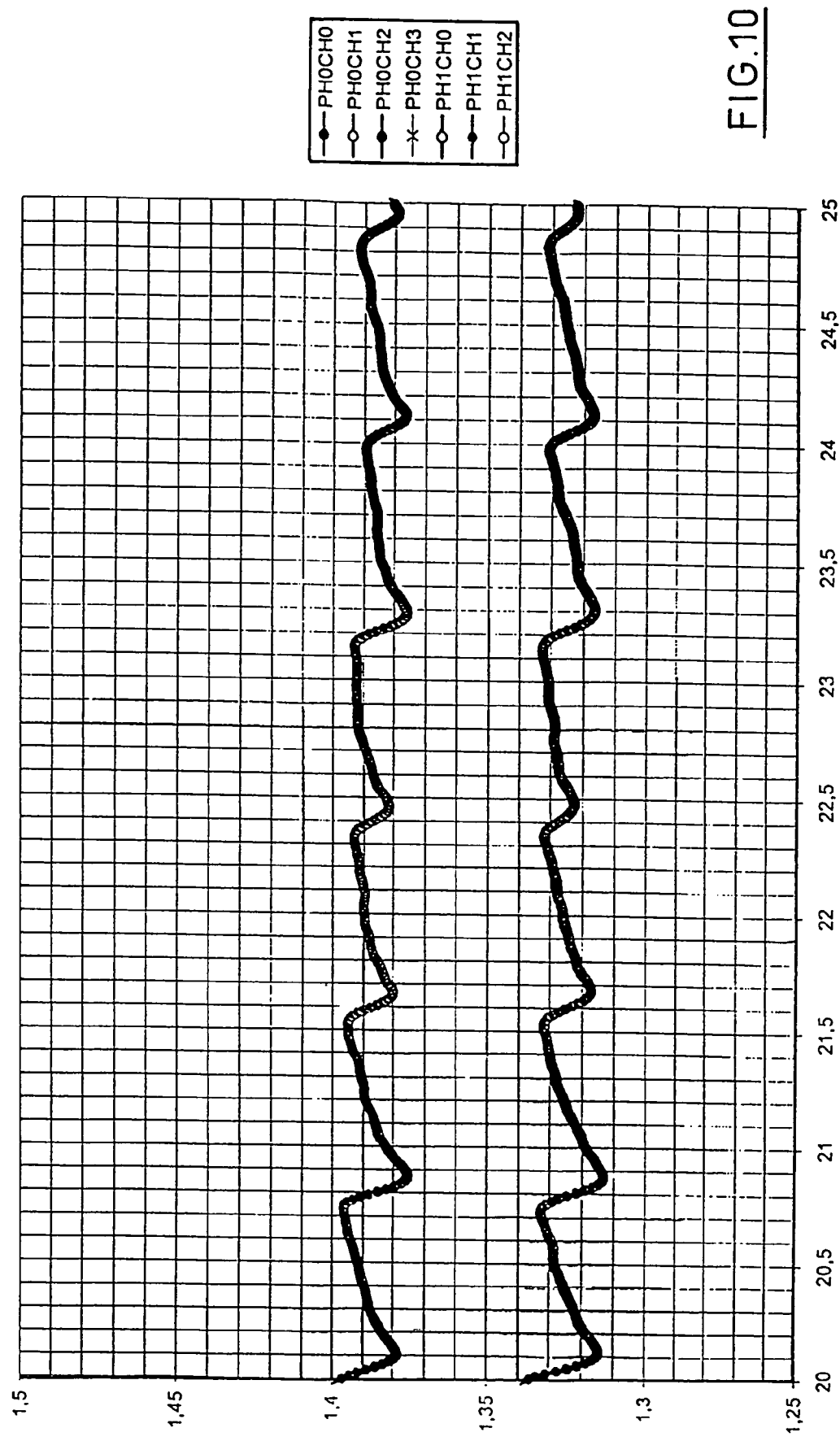
FIG. 10 shows plethysmograms for the three measuring channels for two variables each.

FIG. 4 shows the typical absorption behavior in a measurement of the oxygen saturation of the blood. The absorption intensity (26) is plotted as a function of the given wavelength (27). A first minimum occurs at a wavelength of about 600 nm; there is then another increase to a relative maximum at about 900 nm; and then the curve asymptotically approaches the zero line.

The device in accordance with the invention makes it possible largely to eliminate motion artifacts and sensor relocations, since an automatic calibration to the new optical path length occurs in each case. This makes it possible to use the device even on moving patients and quickly to provide the attending physician a basis for deciding what measures need to be taken. In this regard, it is taken into account that rapid movements lead to an interruption in the flow of measurement values, whereas sensor relocations with phases of relative rest do not.

Depending on the specific application requirements, different wavelengths can be preset. Furthermore, it is also possible to implement different emission characteristics of the emission sources (5, 6, 7). In this regard, the emission characteristics can be tightly bundled, for example, or implemented with a fanned-out radiation lobe.

The individualized patient calibration can be carried out either before the actual performance of the measurement or periodically during the performance of the measurement. Especially a periodic determination in the course of the pulse-spectroscopic measurement is advantageous. This makes it possible to compensate for intended or arterial position changes of the optical sensors (2, 3, 4) or for changes in the application site during the performance of the measurement.

In general, a pulse-spectroscopic measurement offers the advantage that measurement results from tissue and blood can be supplied with high measuring accuracy in a very short time and without invasive methods on the patient. The light energy detected by the sensors (2, 3, 4) has a pulsatile component and an aperiodic component. The pulsatile component is a consequence of the change in the thickness of the blood vessels in correspondence with the cyclically pulsating flow of blood. The aperiodic component is the radiation component that exits after passage through the tissue. The light energy varies as a function of the illumination intensity by the particular emission sources (5, 6, 7) that are selected.

A concrete instrumental realization of the device described in FIGS. 1–3 can occur within different design parameter intervals, depending on the intended application. A permissible transmission wavelength lies within a range of 3 mm to 35 mm, preferably a range of 5 mm to 30 mm, and especially a range of 7 mm to 25 mm.

The number of emission elements is 7, and preferably 4.

The emission elements can be used, e.g., in the form of 4×LED+3×LD, preferably 2×LED+2×LD, and especially 4×LD.

The wavelengths in the area of the emission elements lie at 550 nm to 1,500 nm, preferably 620 nm to 1,350 nm, and especially 660 nm to 1,300 nm.

The solid-angle positions of the emission elements lie in a range of 1° to 179°, preferably 75° to 125°, and especially 85° to 95°.

The emission elements are preferably centered with a primary diode in the center and preferably with secondary diodes on the sides. Basically, however, centering is not necessary.

The LEDs and/or LDs are preferably focused with a plane optical flat and especially preferably with a lens. Basically, however, focusing is not necessary.

The number of detector elements is 2–8, preferably 2–5, and especially 3.

The solid-angle position of the detector elements lies within a range of −89° to +89°, preferably −25° to +35°, and especially −10° to +10°.

The normals to the center of the detector surface are preferably centered with respect to the center emission, and the normals to the sides are preferably centered on secondary emissions.

The size of the detector elements lies within a range of 2 mm$^2$ to 10 mm$^2$, preferably 2 mm$^2$ to 5 mm$^2$, and especially 3 mm$^2$.

Basically, the measuring method of the above general description and the device that has been explained can be used for various applications. Two especially preferred applications are explained in detail below.

Figure 11:
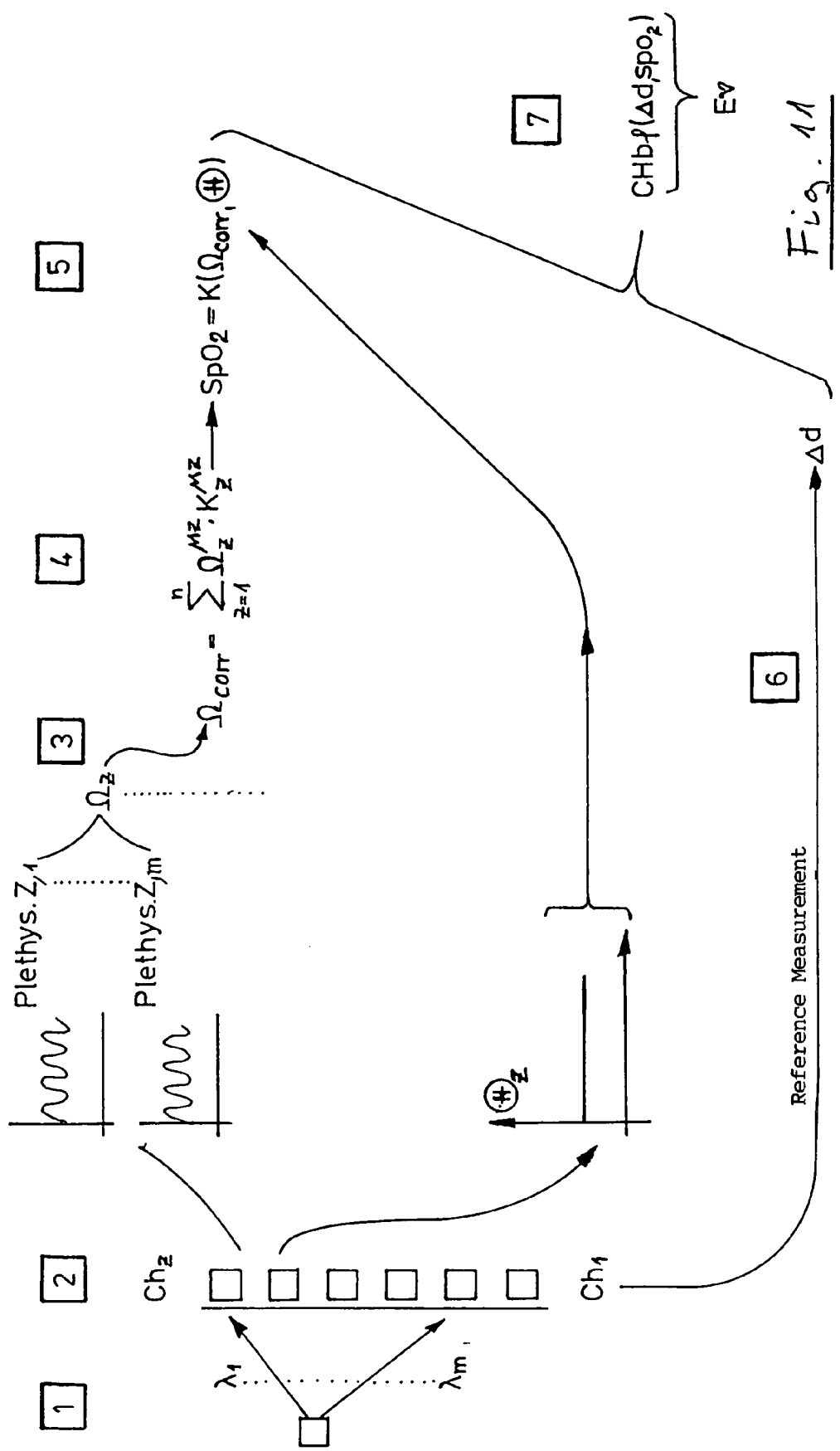
FIG. 11 shows a schematic representation for illustrating the determination of the values for omega, delta d, and the concentration values as a function of the detected measurement values.

In a pulse-oximetric, patient-individualized calibration (PIC), the most important point is that, in contrast to the present state of the art, several plethysmograms are recorded by photoelectric transducers that have a well-defined spatial relationship to one another. The process sequence is described below and is graphically illustrated in FIG. 11.

These plethysmograms are recorded by each photoelectric transducer for different wavelengths of emitted radiation. The wavelengths are taken from the visible (VIS) region and the NIR/IR region of the electromagnetic spectrum.

A measurement variable $\Omega_Z$ is formed for each photodiode Z by linking characteristic properties of these plethysmograms. Using the pulse-oximetric measuring technique, it is possible for a measurement variable $\Omega$ to be determined and for this variable to be assigned to the value of an O$_2$ saturation by a calibration that is defined a priori.

The process sequence in accordance with the invention takes all measurement variables $\Omega_Z$ and combines them into a new corrected measurement variable $\Omega_{Corr}$ by means of a sensor-specific transfer function. In addition, this measurement variable is combined with the tissue-specific differential attenuation $\theta$.

The tissue-specific differential attenuation $\theta$ is a measure of the decrease in radiation intensity within the measurement site. This attenuation is obtained by analysis of the differences of all absolute intensities at all z photoelectric transducers.

The photoelectric transducers are arranged in a geometrically sufficiently well-defined way. Therefore, the changes in the absolute intensities can be attributed to the varied light paths for individual patients.

The differential attenuation $\theta$ follows from the combined absorption and deflection (scattering and refraction) of photons at the measurement site. The components of these individual processes do not have to be separately determined for the present method.

The differential attenuation $\theta$ and the corrected measurement variable $\Omega_Z$ determine the target quantity of the method, namely, the arterial oxygen saturation, by the calibration function of the invention. The following is the PIC correction function:

$$\Omega_{Corr} = f\left(\sum_z K_{1z} \cdot \Theta^{K_{2z}} \Omega_z^{K_{3z}}\right)$$

The variable $\Omega_{Corr}$ represents the resulting measurement variable, which is assigned to the arterial oxygen saturation by the calibration function $saO_2 = g(\Omega_{Corr})$ The factors $K_{1z}$, $K_{2z}$, and $K_{3z}$ are validated and adapted by an empirical (clinical) analysis.

The behavior of the calibration function $g(\Omega_{Corr})$ corresponds to the well-known, empirically determined calibration at the application sites of pulse oximetry.

Another preferred application of the invention is the noninvasive continuous determination of the hemoglobin concentration.

The determination of the hemoglobin concentration is based on the patient-individualized calibration (PIC). Without this calibration, an absolute determination, i.e., a quantity with a physical unit of measure (here [mg/dL]), cannot be performed with sufficient accuracy.

The attenuation of substance concentrations within a tissue can be derived by the method of pulse spectroscopy only from the product of the change in thickness and the substance concentration.

$$\Delta d \cdot C = (d_2 - d_1) \cdot C = \frac{\ln\left(\frac{I_1}{I_2}\right)}{\sum_N \varepsilon(\lambda) \cdot sX}$$

In the above formula:
C: concentration of the desired substance
$\Delta d$: change in thickness of the pulse-spectroscopic target tissue
$I_1$ and $I_2$: VIS/NIR/NR intensities after passage through the tissue
$\varepsilon(\lambda)$: wavelength-dependent absorbances of the substance derivatives X of S
sX: saturation of the substance S with the derivative X
N: number of spectroscopically relevant substances at the site of measurement.

The thickness change in the pulsating vessels is associated with a pulse-cyclical change in transmission. This is the basis of each plethysmogram. The amplitude of plethysmograms is defined by three characteristics:

1. The pulse-cyclical vascular diameter change D;
2. The absorbances $\varepsilon_n(\lambda)$ of the substance concentrations contained in it at the time of measurement; and
3. The modification of the absorbance $\varepsilon_n(\lambda)$ of pulse-cyclical attenuations in the accompanying tissue.

The absorbance $\varepsilon_n(\lambda)$ is differentiated from the vascular thickness change D by an additional NIR/IR emission, i.e., by the so-called reference measurement. In the region of the measurement wavelength, this NIR/IR emission should not experience any appreciable (concentration-dependent) absorption in the blood constituents to be measured. Its absorption should occur primarily in water.

Due to the modification of attenuations in the accompanying tissue, the determination is again made by the differential attenuation $\theta$ introduced under PIC. A determination is thus made of what signal change is produced in the photoelectric transducers by a specific change in absorption.

With the use of the water reference measurement and the differential attenuation $\theta$, the hemoglobin concentration is then calculated from the given conditional equation on the basis of the known relative concentrations (saturations).

$$cHb = f\left(\Delta d, \sum_{n=1}^N [\varepsilon_n(\lambda) \cdot saX_n], \sum_z K \cdot \Theta\right)$$

In the above formula:

Δd: differential thickness change of the pulsating arterial tissue components

N: number of hemoglobin derivatives in the patient

η: counting variable $\epsilon_\eta(\lambda)$: wavelength-dependent spectral extinction of the Hb fraction η

K: VIS/NIR (IR) attenuation for photoelectric transducer No. Z $saX_\eta$: saturation of the total hemoglobin by the fraction η; Example: $X_\eta$=CO, i.e., saCO.

The hemoglobin measurement is thus accessible to a continuous, noninvasive measurement.

The derivatives $saX_\eta$ are determined in a novel way by the use of the PIC methodology. This more exact method of determination is a prerequisite for a sufficiently exact determination of the desired substance concentration cHb.

The likewise novel measurement of the attenuation θ also enters into the conditional equation.

The invention claimed is:

1. Method for controlling a device for measuring quantitative proportions of blood constituents, in which electromagnetic radiation of different radiation frequencies is passed through a blood-containing vessel, and at least a portion of the radiation exiting the vessel is detected by sensors and fed to an evaluating device, wherein at least two radiation detection sensors (2, 3, 4) are positioned a certain distance apart and that the evaluating device is assigned a calibration characteristic curve, which is determined by an individual calibration measurement, in which at least one constant is used as the calibration criterion and is determined from at least one measurement variable (22) detected by the sensors (2, 3, 4), wherein during the measuring procedure a standard calibration function (13) is combined with a scattering determination (14) and the results of the standard calibration function (13) as well as the output value of the scattering determination (14) are combined with each other by a combiner (16) according to an algorithm preset as an individual calibration function, an output value of the comparator (16) is combined with a measurement variable (17) and the combination of the output value of the combiner (16) and the measurement variable (17) yields the respective target quantity (18).

2. Method in accordance with claim 1, wherein at least three sensors (2, 3, 4) are used.

3. Method in accordance with claim 1, wherein the measuring determination is performed in a multiplex operation.

4. Method in accordance with claim 1, wherein electromagnetic radiation in the optical frequency range is used.

5. Method in accordance with claim 1, wherein pulse spectroscopy is used for the measuring determination.

6. Method in accordance with claim 1, wherein spectrophotometry is used for the measuring determination.

7. Method in accordance with claim 1, wherein the spatial scattering of the radiation is determined by measurement technology.

8. Method in accordance with claim 1, wherein the scattering is determined by determining a radiation intensity that deviates from the primary irradiation direction.

9. Method in accordance with claim 1, wherein a periodic calibration is carried out during the performance of the measurement.

10. Method in accordance with claim 1, wherein the scattering is determined by the relationship between the amplitudes of the measured values of the individual sensors (2, 3, 4).

11. Method in accordance with claim 1, wherein an oxygen concentration of the blood is determined.

12. Method in accordance with claim 1, wherein a relative oxygen concentration of the blood is determined.

13. Method in accordance with claim 1, wherein an absolute oxygen concentration of the blood is determined.

14. Device for measuring quantitative proportions of blood constituents, which has at least one emission source for generating electromagnetic radiation and at least one sensor, which detects the transmitted portion of the radiation and is connected with an evaluating device, wherein the evaluating device (10) has at least two sensors (2, 3, 4) and that the evaluating device (10) has an analyzer (11) for determining the angle-dependent scattering of the radiation by evaluating the signals received from the individual sensors (2, 3, 4), wherein a standard calibration function (13) is implemented in an area of the evaluating device (10), the evaluating device (10) having a combiner (16) that is operative to combine results of the standard calibration (13) and an output value of a scattering determination (14) according to an individual calibration function, whereby an output value of the combiner (16) and a measurement variable (17) yields a target value (18).

15. Device in accordance with claim 14, wherein at least three sensors (2, 3, 4) are connected to the evaluating device (10).

16. Device in accordance with claim 14, wherein at least two emission sources (5, 6, 7) are used.

17. Device in accordance with claim 14, wherein at least three emission sources (5, 6, 7) are used.

18. Device in accordance with claim 14, wherein at least one of the emission sources (5, 6, 7) is designed as a light-emitting diode.

19. Device in accordance with claim 14, wherein at least one of the emission sources (5, 6, 7) is designed as a laser diode.

20. Device in accordance with claim 14, wherein at least one of the sensors (2, 3, 4) is designed as a photodiode.

21. Device in accordance with claim 14, wherein the sensors (2, 3, 4) are spaced essentially equal distances apart relative to one another.

* * * * *